(12) United States Patent
Horn

(10) Patent No.: US 6,635,289 B2
(45) Date of Patent: Oct. 21, 2003

(54) METHODS AND COMPOSITIONS FOR RETARDING THE STALING OF BAKED GOODS

(76) Inventor: Merritt C. Horn, 765 Peach Ct., Louisville, CO (US) 80027

( * ) Notice: Subject to any disclaimer, the term of this patent is extended or adjusted under 35 U.S.C. 154(b) by 0 days.

(21) Appl. No.: 09/921,673

(22) Filed: Aug. 3, 2001

(65) Prior Publication Data

US 2002/0058086 A1 May 16, 2002

Related U.S. Application Data

(63) Continuation-in-part of application No. 09/377,678, filed on Aug. 19, 1999, now abandoned.

(51) Int. Cl.$^7$ ................................................. A21D 8/04
(52) U.S. Cl. ........................... 426/20; 426/64; 426/549
(58) Field of Search ........................... 426/18, 61, 549, 426/98, 64, 20, 28; 435/202, 203, 204, 187, 188, 178, 182

(56) References Cited

U.S. PATENT DOCUMENTS

| | | | | |
|---|---|---|---|---|
| 2,642,376 A | * | 6/1953 | Gale et al. ................... | 435/188 |
| 3,527,644 A | * | 9/1970 | Landfried et al. ............. | 426/20 |
| 3,561,975 A | | 2/1971 | Luebering et al. ............. | 99/94 |
| 4,116,772 A | | 9/1978 | Vidal et al. ................... | 195/64 |
| 5,059,430 A | * | 10/1991 | Bowles ........................ | 426/20 |

FOREIGN PATENT DOCUMENTS

| | | |
|---|---|---|
| GB | 1544499 | 4/1979 |
| WO | 98/32336 | 7/1998 |

OTHER PUBLICATIONS

Matz, S. Chapter: "Mixers and Mixing", Bakery Technology and Engineering, 2$^{nd}$ edition; pp. 308–311, copyright 1972 by the Avi Publishing Company.*

* cited by examiner

*Primary Examiner*—Keith Hendricks
(74) *Attorney, Agent, or Firm*—Steven C. Petersen; Sarah O'Rourke; Hogan & Hartson LLP

(57) ABSTRACT

The present invention provides novel baked goods having incorporated therein a delivery vehicle that provides protection to an alpha-amylase enzyme from thermal denaturation and continuously releases the alpha-amylase enzyme during, and following the baking process. Essentially, dry, food-grade alpha-amylase particles are mixed with a food grade lipid in a quantity sufficient to envelop the alpha-amylase particles thereby forming a loaded delivery vehicle or enveloped alpha-amylase. The enveloped alpha-amylase is subsequently added to a dough comprising flour, water, and other dough forming ingredients near the end of the mix cycle. Once the enveloped alpha-amylase is incorporated, the dough continues through the normal production process for that particular baked product. The food grade lipid enveloping the alpha-amylase provides thermal protection to the enzyme. No other production or packaging modifications need be made.

20 Claims, No Drawings

METHODS AND COMPOSITIONS FOR RETARDING THE STALING OF BAKED GOODS

RELATED APPLICATIONS

This is a Continuation-in-Part application of U.S. patent application Ser. No. 09/377,678, filed Aug. 19, 1999, now abandoned, and entitled "Methods and Compositions for Retarding the Staling of Baked Goods," which is incorporated herein by reference.

BACKGROUND OF INVENTION

1. Field of the Invention

The present invention relates to a method for retarding the staling of baked goods, and more particularly to a method for achieving the thermal protection and sustained release of a certain enzyme throughout a baked good during and following the baking process.

2. Description of the State of Art

The phenomenon of bread staling has been studied extensively and a variety of theories have been presented. It is now generally accepted that staling is due to a gradual transition of starch from an amorphous structure to a partially crystalline state. This increase in starch crystallinity, also referred to as retrogradation, is caused by an intermolecular or intramolecular association via hydrogen bonding of the two polysaccharides, amylose and amylopectin, which comprise starch granules.

Amylose is made up largely of unbranched chains of D-glucose units (100–1,400 units) which are joined together by alpha-(1,4)-glucosidic bonds. Retrogradation of amylose is rapid due to the ease of alignment of the linear molecules. Amylopectin is the main constituent of starch and, like amylose, it is also constructed from D-glucose units, but in the case of amylopectin they are assembled in shorter, rather bush like, branched chains, containing only 20–25 units of D-glucose. The links in the chain are alpha-(1,4)-glucoside bonds, while the branching points involve alpha-(1,6)-glucosidic bonds. The branched structure of amylopectin interferes with molecular alignment, and consequently amylopectin retrogradation occurs at a much slower rate.

During baking, starch granules swell and absorb moisture, but gelatinization is not complete because of limited water availability. As the granules swell, amylose and to a lesser extent amylopectin diffuse from the granules into the interstitial volume. The solubilized linear molecules retrograde rapidly and form a crystalline network which in combination with the gluten matrix form the characteristic "crumb set" or structure of bread and other baked goods.

Staling of baked goods is generally defined as an increase in crumb firmness and a corresponding loss in product freshness. Flavor, aroma, texture, perceived moisture level, and other product characteristics are also negatively affected as staling proceeds. The staling process begins as soon as baking is complete. Amylopectin remains mostly in the starch granule and retrogrades slowly during product storage. Retrogradation occurs by intermolecular and intramolecular association of linear segments, and to a lesser extent between amylopectin and amylose at the interface of the starch granules and the interstitial volume. As amylopectin retrogradation proceeds, a three-dimensional crystalline structure is formed slowly, causing an increase in firmness, or staling.

Factors that control the rate of staling include time, temperature, moisture level, and the presence of additives such as emulsifiers (crumb softeners). Rate of staling shows a linear response with time, but can be minimized by maintaining the maximum allowable moisture in the product or by storage at warm (room temperature or higher) or cold (below freezing) temperatures. Refrigeration enhances staling since the rate of retrogradation is optimal at cold temperatures just above freezing.

Staling eventually causes a product to become unacceptable at the retail or consumer level. It is estimated that 3–5% of all baked goods produced in the United States are discarded due to a loss in freshness. The value of discarded baked goods has been estimated to exceed $1 billion annually in the U.S. alone. It is obvious that prolonging the freshness of baked goods by retarding staling would be a benefit to the producer, retailer, and consumer.

A common practice within the baking industry to retard staling is to add chemical emulsifiers to the dough formulation. About 12–15 million pounds of distilled monoglyceride and 20–25 million pounds of mono- and diglycerides are used annually in the baking industry for this purpose. However, while chemical emulsifiers do produce a softer bread, they are only partially effective in reducing bread staling because they appear to function by creating softer bread out of the oven rather than by acting upon the mechanism of starch retrogradation directly. That is, the bread still stales at about the same rate, but it starts from a softer loaf and so reaches unacceptable firmness later than untreated bread. As can be surmised from this description, a limiting factor in surfactant use is the initial softness of the loaf: both bakery production processes (such as slicing), and consumer preferences require a certain level of firmness in bread which sets a limit to surfactant use.

In addition to the usage of chemical emulsifiers, enzymes which modify the starch responsible for staling are also used for increasing shelf-life of baked goods. Enzymatic techniques for reducing firming in baked goods have been studied for years, and the beneficial action of enzymes has been recognized. However, commercially available enzymes have been in the past either only marginally effective or they produced offsetting negative effects in product quality that precluded widespread use.

The amylases are a specific type of enzyme which hydrolyze the glycosidic linkages in polyglucans, and for this reason are grouped with hydrolases. The specific amylases of special interest to bakers are alpha-(1,4)-glucan glucanohydrolase (or alpha-amylase) and alpha-(1,4)-glucan maltohydrolase (or beta-amylase) derived from various cereal and microbial sources. The amylases are widely distributed in nature, occurring in many animal tissues, higher plants, molds, yeast and bacteria. Until recently, the only alpha-amylases used in baking were cereal enzymes from barley malt, fungal enzymes derived mainly from *Aspergillus oryzae*, and bacterial enzymes derived from *Bacillus subtilis*. Depending on their origin, alpha-amylases show measurable differences in certain properties, such as pH and temperature optima, thermostability, and resistance to inactivation by acidity. They are simple crystallizable proteins that do not require the presence of coenzymes for their activity. Because of their protein nature, they exhibit a general heat lability. Table 1, shown below, demonstrates the thermostability of alpha-amylases from various sources.

TABLE 1

| Temperature | | Percent of Enzyme Activity | | |
|---|---|---|---|---|
| °C. | °F. | Fungal | Barley Malt | Bacterial |
| 65 | 149 | 100 | 100 | 100 |
| 70 | 158 | 52 | 100 | 100 |
| 75 | 167 | 3 | 58 | 100 |
| 80 | 176 | 1 | 25 | 92 |
| 85 | 189 | — | 1 | 58 |
| 90 | 194 | — | — | 22 |
| 95 | 203 | — | — | 8 |

The data in Table 1 demonstrates that fungal alpha-amylase is quite heat labile and is inactivated rapidly at temperatures above 149° F. (65° C.). A temperature above 167° F. (75° C.) is required for a comparable inactivation of cereal alpha-amylase. Bacterial alpha-amylase is the most stable and shows little loss of activity at temperatures up to 185° F. (85° C.).

As the temperature of the dough rises during baking, starch is gelatinized over the range of 140° to 167° F. (60° to 75° C.), rendering it susceptible to amylase attack. Alpha-amylase specifically hydrolyzes the alpha-(1,4)-glycosidic linkages in starch at random points within the amylose and amylopectin molecules. Some alpha-amylases are capable of hydrolyzing linkages within the amorphous regions of the starch matrix during baking. Under the proper conditions, this limited degree of hydrolysis is sufficient to disrupt the starch network and reduce the rate of staling.

Barley malt is often added directly to wheat flour at the mill to standardize alpha-amylase activity. Standardization enhances production of fermentable sugars from damaged starch, increases yeast growth and gas production, and improves dough handling and proofing. Barley malt also improves finished product properties such as color, grain, texture, and flavor. However, since barley malt retains much of its activity over the temperature range of starch gelatinization, it is important to avoid an excess of cereal amylase to prevent the undesireable result of gummy, sticky crumb. Shelf-life, however is not improved.

Bacterial alpha-amylase enzyme most often refers to enzymes made from *Bacillus subtilis*, and are able to inhibit staling by hydrolysing glycosidic linkages within the amorphous areas of gelatinized starch. The enzyme is most active at a pH of about 7 and a temperature of about 75 to 80° C.

One enzymatic approach to retarding bread staling is disclosed in U.S. Pat. No. 2,615,810 to Stone and involves the use of a heat-stable bacterial alpha-amylase enzyme to attack gelatinized starch granules during baking. A refinement to Stone's approach is described in U.S. Pat. No. 4,299,848 to DeStefanis, et al. which discloses a process for the inactivation of the proteolytic enzymes present in commercially available heat stable bacterial alpha-amylase enzyme preparations obtained from extracts of *Bacillus subtilis, Bacillus stearothermophilus* or other microbial sources. In a further refinement, U.S. Pat. No. 4,654,216 to Carroll, et al. discloses the addition of an enzyme mixture of heat stable bacterial alpha-amylase and a pullulanase to dough in proportions of from 0.25 to 5 SKB (alpha-amylase units) and 5 to 75 PUN (debranching enzyme units) per 100 grams of flour.

G. Bussiere, et al. in "The Utilization of Alpha-Amylase and Glucoamylase in Industrial Baking Technology," *Annales De Technologie Agricole*,vol. 23 (2), pp. 175–189 (1974) disclose studies on the role of heat stable bacterial alpha-amylases derived from *Bacillus subtilis* in bread making technology. Bussiere, et al. teach that heat stable alpha-amylases of bacterial origin are effective in retarding staling, but produce a sticky bakery product when a dosage of 2.5 SKB units or more per 100 grams of flour is used.

A drawback of the Stone, DeStefanis, et al., Carroll, et al., and Bussiere, et al. approaches is the tendency of heat stable bacterial alpha-amylases to remain active too long during baking and to cause gumminess in the finished product. As a result, these approaches require a degree of control over dosages and enzyme ratios which may be impractical to apply commercially.

Further attempts to improve the action of bacterial amylases have focused on genetic manipulation of the naturally occurring bacteria to create a bacteria which produces alpha-amylase which is less thermostable. Some of these products, such as Novamyl® from Novo Nordisk BioChem (Franklinton, N.C.) have partially overcome the limitations of naturally occurring bacterial amylase and have achieved some acceptance in the industry, but finished product quality still needs improvement and the reliance on genetic modification makes such products unacceptable for use in "Certified Organic" foods (as defined by the California Organic Foods Act of 1990) which constitutes a significant developing market for baked goods.

Fungal alpha-amylase enzymes are effective in partially hydrolysing damaged starch and are often added to flour, in the same manner as barley malt, to develop desirable properties for baking. However, conventional fungal amylases exhibit limited thermostability and are, for the most part, inactivated prior to the onset of starch gelatinization during baking since their optimum temperature range is only 50–55° C. As a result, fungal alpha-amylases have little effect on amylopectin hydrolysis and do not exhibit significant anti-staling activity.

In an attempt to provide a fungal alpha-amylase that exhibits anti-staling activity, Cole in his U.S. Pat. No. 4,320,131 discloses that the thermal stability of fungal alpha-amylase is substantially increased by dispersing aqueous solutions of the enzyme in concentrated sugar solutions. This procedure reportedly protects the enzyme from thermal denaturation, allowing it to retain activity during baking. Use of the stabilized enzyme in conjunction with the proper emulsifier in a carefully controlled process reputedly reduces product firmness, although use of the enzyme alone is not effective. However, the processing and ingredient changes required make this approach unsuitable for a number of bakery applications.

Livermore, et al., in PCT Application WO 98/32336, disclose a latent enzyme preparation for use as a bread improver to improve the quality of a loaf of bread. The latent enzyme is prepared by coating a microparticulate form of alpha-amylase with a fat having a slip melting point of at least 35° C. According to the method of Livermore et al., the required level of encapsulation of the enzyme with the fat is less than 100%, and in some cases is less than 50%. Due to the choice of fat used by Livermore et al. to coat the enzyme, the enzyme is released into the dough during the proofing stage of the bread making process. That is, active, unprotected enzyme is release into the dough during the proving stage and early in the baking process. It is known that fungal alpha-amylase becomes heat-denatured at temperatures around 50° C. Therefore, since the alpha-amylase in the Livermore et al. preparation is no longer coated by the fat once the dough enters the baking stage, the alpha-amylase is consequently denatured during the baking stage, which is typically done at temperatures much higher than 50° C. As a result, the baked good produced by the method of Livermore et al. does not contain an active enzyme.

There is still a need, therefore, for a method and composition produced therefrom which utilizes alpha-amylase enzymes in a manner that is suitable in a number of bakery applications and which achieves an acceptable baked good having an extended shelf-life.

SUMMARY OF THE INVENTION

Accordingly, the present invention provides a method for retarding the staling of baked goods and for extending the shelf life of baked goods.

More specifically, this invention provides a delivery vehicle for alpha-amylase enzymes which protect the enzyme from thermal denaturation and provides for a sustained release of the enzyme.

This invention further provides a delivery vehicle containing an active alpha-amylase enzyme for combining with ingredients for the preparation of a baked good, wherein the delivery vehical releases active alpha-amylase enzyme into the baked good to reduce the staling rate of the baked good.

This invention further provides a baked good having incorporated within it a delivery vehicle which continuously releases an active alpha-amylase enzyme during the baking process and in the baked good.

The baked goods of this invention and the methods provided for preparing such baked goods meet the requirements of the California Organic Foods Act of 1990 or any comparable act.

Additional objects, advantages and novel features of this invention shall be set forth in part in the description that follows, and in part will become apparent to those skilled in the art upon examination of the following specification or may be learned by the practice of the invention. The objects and advantages of the invention may be realized and attained by means of the instrumentalities, combinations, and methods particularly pointed out in the appended claims.

To achieve the foregoing and other objects and in accordance with the purposes of the present invention, as embodied and broadly described therein, the method of this invention results in a baked good comprising flour, water, other dough-forming ingredients, and an effective quantity of a loaded delivery vehicle to enhance the shelf-life of the baked good, wherein the loaded delivery vehicle comprises alpha-amylase particles encapsulated with a food grade lipid.

DETAILED DESCRIPTION OF THE PREFERRED EMBODIMENT

The present invention provides novel baked goods which have incorporated therein a delivery vehicle which provides protection of an active alpha-amylase enzyme from thermal denaturation, and which continuously releases the active alpha-amylase enzyme during the baking process and in the baked good products. Essentially, dry, food-grade alpha-amylase particles in powder form are mixed with a food grade lipid in a quantity sufficient to envelop all or substantially all of the alpha-amylase particles, thereby forming a loaded delivery vehicle (i.e., enveloped alpha-amylase particles). The enveloped alpha-amylase particles are subsequently combined with dough containing ingredients such as flour and water near the end of the mix cycle. Other dough-forming ingredients which may be added to the dough include, but are not limited to, yeast, sugar, shortening, milk powder, salt. Once the enveloped alpha-amylase is incorporated, the dough continues through the normal production process for that particular baked product. The food grade lipid enveloping the alpha-amylase provides thermal protection to the enzyme during the baking process. No other production or packaging modifications need be made.

The present invention begins with the production of a delivery vehicle containing an active alpha-amylase enzyme. As used herein, "delivery vehicle" refers any of the oils disclosed herein that encapsulates or envelopes an enzyme particle and which provide thermal protection of the enzyme during the baking stage of preparing a baked good. As used herein, "enzyme particle" refers to a single protein unit or molecule. For example, the term "alpha-amylase particle" is intended to refer to one alpha-amylase protein molecule.

In one embodiment of this invention, the alpha-amylase is a fungal alpha-amylase. Alternatively, a variety of alpha-amylases are available in the industry which are suitable for use in this invention, including, but not limited to, bacterial-derived and cereal-derived types. The fungal alpha-amylase disclosed herein is in powder form, can be obtained from Enzyme Development Corporation, N.Y., N.Y. and is sold under the name ENZECO® Fungal Alpha-Amylase Powder.

To prepare the enveloped alpha-amylase particles according to this invention, alpha-amylase particles, such as fungal alpha-amylase in powder form, are contacted with a food grade lipid, discussed in further detail below, in sufficient quantity so as to suspend all of the fungal alpha-amylase particles. Surprisingly, the inventor of the instant invention discovered that when alpha-amylase in microparticulate form is used, not all of the individual alpha-amylase particles are encapsulated. This is due to the fact that microparticulates are aggregates of enzyme particles, and therefore the lipid cannot access and thus encapsulate each individual particle in the aggregate. However, the inventor discovered that when the powdered form of alpha-amylase was used, 100% or at least substantially all of the enzyme particles are coated with the lipid. By "substantially all", it is meant that the majority of the enzyme particles are coated with the lipid.

The activity of fungal alpha-amylase can be expressed in terms of SKB units, and the preferred level of activity is that which is provided by about 200–5,000 SKB units per pound of formula flour. However, both lesser and greater amounts are satisfactory. When very high levels, such as in excess of 200,000 SKB units of enzyme are used, no detrimental effects are noted, but there is a decided leveling off of beneficial enzyme activity. Hence, from the cost standpoint there is a practical upper limit of enzyme levels. At less than 200 SKB units, it is difficult to appreciate the improved effects, and therefore such a level may be considered a practical lower limit, and about 5,000 SKB units may be considered a preferred usage level.

Food grade lipids, as used herein, may be any naturally organic compound that is insoluble in water but is soluble in non-polar organic solvents such as hydrocarbon or diethyl ether. The food grade lipids preferable utilized in the present invention include, but are not limited to, triglycerides either in the form of fats or oils which are either saturated or unsaturated. Examples of fatty acids and combinations thereof which make up the saturated triglycerides utilized in the present invention include, but are not limited to, butyric (derived from milk fat), palmitic (derived from animal and plant fat), and/or stearic (derived from animal and plant fat). Examples of fatty acids and combinations thereof which make up the unsaturated triglycerides utilized in the present invention include, but are not limited to, palmitoleic (derived from animal and plant fat), oleic (derived from animal and plant fat), linoleic (derived from plant oils), and/or linolenic (derived from linseed oil). Other food grade lipids which are contemplated and within the scope of the present invention include, but are not limited to, monoglycerides and diglycerides derived from the triglycerides discussed above, phospholipids and glycolipids.

The food grade lipid, preferably in the liquid form, is contacted with a powdered form of the alpha-amylase particles in such a fashion that the lipid material covers at least a portion of the surface of at least a majority, and preferably 100% of the alpha-amylase particles. Thus, each alpha-amylase particle is individually enveloped in the lipid. In the preferred embodiment of the present invention, all or substantially all of the particles of alpha-amylase are provided with a thin, continuous, enveloping film of lipid. This can be accomplished by first pouring a quantity of lipid into a container and then slurrying the alpha-amylase so that the lipid thoroughly wets the surface of each alpha-amylase particle. After a short period of stirring, the enveloped alpha-amylase particles, carrying a substantial amount of the lipids on their surfaces, are recovered. The thickness of the coating so applied to the particles of alpha-amylase can be controlled by selection of the type of lipid used and by repeating the operation in order to build up a thicker film, when desired.

The storing, handling and incorporation of the loaded delivery vehicle of the present invention is most conveniently accomplished by means of a packaged mix. Preferably, the packaged mix comprises the enveloped alpha-amylase. However, it is within the teachings of this invention that the packaged mix may further contain additional ingredients as required by the manufacturer or baker. After the enveloped alpha-amylase has been incorporated into the dough, the baker continues through the normal production process for that product.

The advantages of enveloping the alpha-amylase are two-fold. First, it has been discovered that the food grade lipid protects the enzyme from thermal denaturation during the baking process for those enzymes that are heat labile, such as the fungal alpha-amylases. Consequently, while the alpha-amylase is stabilized and protected during the proving and baking stages, it is released from the protective coating in the final baked good product, where it hydrolyzes the glucosidic linkages in polyglucans. Surprisingly, the second advantage is the loaded delivery vehicle provides a sustained release of the active enzyme into the baked good. That is, following the baking process, active alpha-amylase is continually released from the protective coating at a rate which counteracts, and therefore reduces the rate of, staling mechanisms. While not wishing to be bound by any theory, the active enzyme may be released from the lipid coating by any number of mechanisms, including eventual breakdown of the lipid coating. The exact mechanism of release is not critical to this invention. What is important is that the method of this invention provides a method of protecting the active enzyme throughout the mixing, proving, and baking stages so as to provide a baked good which contains a protected active enzyme. Accordingly, the baked goods produced by the methods of this invention contain an active enzyme which is released into the baked good over a period of time, thereby reducing the staling rate of the baked good.

In general, the amount of lipid applied to the alpha-amylase particles can vary from a few percent of the total weight of the alpha-amylase to many times that weight, depending upon the nature of the lipid, the manner in which it is applied to the alpha-amylase particles, the composition of the dough mixture to be treated, and the severity of the dough-mixing operation involved.

The loaded delivery vehicle (i.e., the lipid-enveloped enzyme) is added to the ingredients used to prepare a baked good in an amount that is effective in extending the shelf-life of the baked good. The baker computes the amount of enveloped alpha-amylase, prepared as discussed above, that will be required to achieve the desired anti-staling effect. The amount of the enveloped alpha-amylase required is calculated based on the concentration of enzyme enveloped and on the proportion of alpha-amylase to flour specified by this invention. A wide range of concentrations has been found to be effective, although, as has been discussed, observable improvements in anti-staling do not correspond linearly with the alpha-amylase concentration, but above certain minimal levels, large increases in alpha-amylase concentration produce little additional improvement. The alpha-amylase concentration actually used in a particular bakery production could be much higher than the minimum necessary in order to provide the baker with some insurance against inadvertent under-measurement errors by the baker. The lower limit of enzyme concentration is determined by the minimum anti-staling effect the baker wishes to achieve, and is not integral to the invention itself.

A typical and satisfactory recipe according to the present invention is provided for in Table II below.

TABLE II

| Ingredient | Amount added to dough batch containing 100 lbs. of flour |
|---|---|
| Canola (Rapeseed oil) (lipid) | 1 g |
| fungal alpha-amylase | 25,000 SKB units |

A typical method of preparing a baked good according to the method of this invention comprises:
  a) preparing lipid-coated alpha-amylase particles, wherein substantially 100 percent of the alpha-amylase particles are coated;
  b) mixing a dough containing flour;
  c) adding the lipid-coated alpha-amylase to the dough before the mixing is complete and terminating the mixing before the lipid coating is removed from the alpha-amylase;
  d) proofing the dough; and
  e) baking the dough to provide the baked good, wherein the alpha-amylase is inactive during the mixing, proofing and baking stages and is active in the baked good.

Thus, the enveloped alpha-amylase is preferably added to the dough near the end of the mix cycle. A significant feature of the method of this invention is that the enveloped alpha-amylase is added at a point in the mixing stage which allows sufficient distribution of the enveloped alpha-amylase thoughout the dough, however, the mixing stage is terminated before the protective coating becomes stripped from the alpha-amylase particle(s). Depending on the type and volume of dough, and mixer action and speed, anywhere from one to six minutes or more might be required to mix the enveloped alpha-amylase into the dough, but two to four minutes is average. Thus, there are several variables here that determine the precise procedure. First, the quantity of enveloped alpha-amylase must have a total volume sufficient to allow the enveloped alpha-amylase to be spread throughout the dough mix. If the preparation of enveloped alpha-amylase is highly concentrated, additional oil may need to be added to the pre-mix before the enveloped alpha-amylase is added to the dough. Recipes and production processes may require specific modifications; however, good results have been achieved when 25% of the oil specified in a bread dough formula is held out of the dough and is used as a carrier for a concentrated enveloped alpha-amylase when added near the end of the mix cycle. In bread or other baked goods, recipes which have extremely low fat content (such as french breads), it has been found that an enveloped alpha-amylase mixture of approximately 1% of the dry flour weight is sufficient to properly admix the enveloped alpha-amylase with the dough, but the range of percentages that may work is extremely wide and is dependent on the formula, finished product, and production methodology requirements of the individual baker rather than upon any known limitations of the invention. Second, the enveloped alpha-amylase suspension must be added to the mix with enough time remaining in the mix cycle for complete mixture into the dough, but not so early that excessive mechanical action will strip the protective lipid coating from a large proportion of the enveloped alpha-amylase particles.

In another embodiment, bacterial alpha-amylase (BAA) is added to the lipid-coated enzyme particles. BAA is known to reduce bread to a gummy mass due to its excessive thermostability and retained activity in the fully baked loaf of bread. However, it has been found that when BAA is incorporated into the protected enzyme product of this invention, substantial additional anti-staling protection is obtained, even at very low BAA dosage levels. For example, BAA dosages of 150 RAU (Reference Amylase Units) per 100 pounds of flour have been found to be effective. Preferably between about 50 to 2000 RAU of BAA is added to the lipid-coated enzyme product. This low BAA dosage level, combined with the ability of the protective coating to keep enzyme in the fully-baked loaf from free contact with the starches, (except when water vapor randomly releases the enzyme from its coating) helps to achieve very high levels of anti-staling activity without the negative side-effects of BAA.

The lipid-coated active alpha-amylase enzymes prepared according to the method of this invention significanly reduce the staling rate of baked goods. For example, an analysis of the staling rate experienced by a wholesale bread company over a 60 month period illustrates the economic benefit of this invention. By incorporating a lipid-coated enzyme of this invention into baked goods according to the method of this invention, the shelf lives of the baked goods were extended such that the return rate on the baked goods was reduced from 16.1% of gross sales for the two years prior to incorporation of the lipid-coated enzyme, to 8.3% after incorporation of the lipid-coated enzyme.

EXAMPLE 1

In a series of tests, Fungal Alpha Amylase (FAA) was protected according to the method of this invention and was subjected to various elevated temperatures. In each instance, the sample was held above the specified temperature for five (5) minutes and then was allowed to cool. After cooling, the protected enzyme was tested for activity by mixing small extracts into cornstarch gel cubes to observe the rate of liquifaction. As summarized in Table 3, thermal protection of the lipid-coated enzyme was demonstrated at temperatures well above those at which FAA is normally denatured, and also above the normal peak temperature reached within a loaf of bread during baking.

TABLE 3

Average Time to Liquefaction

| | Test Temperature | | | | |
|---|---|---|---|---|---|
| | 190° F. | 200° F. | 210° F. | 220° F. | 250° F. |
| Time (Minutes) (Protected Enzyme) | 0.7 | 1 | 1.3 | 2.2 | — |
| | 0.6 | 0.7 | 1.4 | 2.6 | — |
| | 0.8 | 0.7 | 1.1 | 1.9 | — |
| | 0.7 | 0.9 | 1 | 2.4 | — |
| Average (Minutes) | 0.7 | 0.8 | 1.2 | 2.3 | — |
| Control (Unprotected Enzyme) | No liquefaction at any tested temperature | | | | |

The foregoing description is considered as illustrative only of the principles of the invention. Furthermore, since numerous modifications and changes will readily occur to those skilled in the art, it is not desired to limit the invention to the exact construction and processes shown as described above. Accordingly, all suitable modifications and equivalents may be resorted to falling within the scope of the invention as defined by the claims which follow. The words "comprise," "comprises," "comprising," "include," "including," and "includes," when used in this specification and in the following claims are intended to specify the presence of stated features, integers, components, or steps, but they do not preclude the presence or addition of one or more other features, integers, components, steps, or groups thereof.

The embodiments of the invention in which an exclusive property or privilege is claimed are defined as follows:

1. A method of preparing a baked good, comprising:
   (a) preparing a loaded delivery vehicle comprising lipid-coated alpha-amylase particles, derived from either a cereal or from both a fungus and a bacteria, wherein substantially 100 percent of said alpha-amylases particles are coated;
   (b) mixing a dough containing flour;
   (c) adding said lipid coated alpha-amylase particles loaded delivery vehicle to said dough before said mixing is complete and terminating said mixing before said the lipid coating is removed from said alpha-amylase;
   (d) proofing said dough;
   (e) baking said dough to provide said baked good.

2. The method of claim 1, wherein said loaded delivery vehicle the amount of said lipid-coated alpha-amylase particles is added in an amount effective to reduce the staling of said baked good subsequent to said baking step.

3. The method of claim 1, wherein said fungal alpha-amylase is derived from *Aspergillus oryzae.*

4. The method of claim 1, wherein said cereal alpha-amylase is derived from barley malt.

5. The method of claim 1, wherein said bacterial alpha-amylase is derived from *Bacillus subtilis.*

6. The method of claim 1, wherein said bacterial alpha-amylase is present in an amount between about 50 and about 200 SKB units per 100 pounds of flour.

7. The method of claim 1, wherein said fungal alpha-amylase is present in an amount of at least 5,000 SKB units per 100 pounds of flour.

8. A method for preparing a baked good comprising forming a mixture of flour, water, and a quantity of a loaded delivery vehicle comprising lipid-coated alpha-amylase wherein said alpha-amylase is derived from either a cereal or from both a fungus and a bacteria; mixing said flour mixture, and baking said flour mixture.

9. The method of claim 8, wherein said fungal alpha-amylase is derived from *Aspergillus oryzae*.

10. The method of claim 8, wherein said cereal alpha-amylase is derived from barley malt.

11. The method of claim 8, wherein said bacterial alpha-amylase is derived from *Bacillus subtilis*.

12. The method of claim 8, wherein said bacterial alpha-amylase is present in an amount between about 50 and about 200 SKB units per 100 pounds of flour.

13. The method of claim 8, wherein said fungal alpha-amylase is present in an of at least 5,000 SKB units per 100 pounds of flour.

14. A baked good comprising flour, water, and a loaded delivery vehicle comprising either a lipid-coated cereal alpha-amylase or a fungal alpha-amylase in combination with a bacterial alpha alpha-amylase combination of a lipid-coated fungal alpha-amylase and a lipid-coated bacterial alpha-amylase.

15. The baked good of claim 14, where in said cereal lipid-coated alpha-amylase or said combination of fungal and bacterial lipid-coated alpha-amylase is present in an amount effective to reduce the staling of said baked good subsequent to baking.

16. The baked good of claim 14, wherein said fungal alpha-amylase is derived from *Aspergillus oryzae*.

17. The baked good of claim 14, wherein said cereal alpha-amylase is derived from barley malt.

18. The baked good of claim 14, wherein said bacterial alpha-amylase is derived from *Bacillus subtilis*.

19. The baked good of claim 14, wherein said bacterial alpha-amylase is present in an amount between about 50 and about 200 SKB units per 100 pounds of flour.

20. The baked good of claim 14, wherein said fungal alpha-amylase is present in an amount of at least 5,000 SKB units per 100 pounds of flour.

* * * * *